United States Patent

Coburn et al.

[11] Patent Number: 5,846,978
[45] Date of Patent: Dec. 8, 1998

[54] HIV PROTEASE INHIBITORS USEFUL FOR THE TREATMENT OF AIDS

[75] Inventors: Craig A. Coburn, Skippack; Mark E. Fraley, North Wales; M. Katharine Holloway; Randall W. Hungate, both of Lansdale; Kristine Prendergast, Bala Cynwyd, all of Pa.

[73] Assignee: Merck & Co., Inc., Rahway, N.J.

[21] Appl. No.: 850,359

[22] Filed: May 2, 1997

Related U.S. Application Data

[60] Provisional application No. 60/016,695 May 2, 1996.
[51] Int. Cl.⁶ .................... A61K 31/435; C07D 221/22
[52] U.S. Cl. ............................................. 514/299; 546/112
[58] Field of Search ..................... 514/616, 622, 514/231.5, 299; 546/112

[56] References Cited

U.S. PATENT DOCUMENTS 5,413,999 5/1995 Vacca et al. .......................... 514/231.5

FOREIGN PATENT DOCUMENTS 0337714 10/1989 European Pat. Off. .

Primary Examiner—Shean C. Wu
Attorney, Agent, or Firm—Kenneth R. Walton; Melvin Winokur

[57] ABSTRACT

Compounds such as

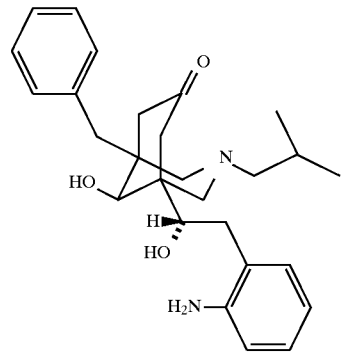

or pharmaceutically acceptable salts thereof, are HIV protease inhibitors. These compounds are useful in the prevention or treatment of infection by HIV and in the treatment of AIDS, either as compounds, pharmaceutically acceptable salts, pharmaceutical composition ingredients, whether or not in combination with other antivirals, immunomodulators, antibiotics or vaccines. Methods of treating AIDS and methods of preventing or treating infection by HIV are also described.

13 Claims, No Drawings

HIV PROTEASE INHIBITORS USEFUL FOR THE TREATMENT OF AIDS

This application claims the benefit of U.S. Provisional application Ser. No. 60/016,695, filed May 2, 1996.

This application is related to U.S. Ser. No. 08/850,360, filed May 2, 1997.

The present invention is concerned with compounds which inhibit the protease encoded by human immunodeficiency virus (HIV) or pharmaceutically acceptable salts thereof and are of value in the prevention of infection by HIV, the treatment of infection by HIV and the treatment of the resulting acquired immune deficiency syndrome (AIDS). It also relates to pharmaceutical compositions containing the compounds and to a method of use of the present compounds and other agents for the treatment of AIDS and viral infection by HIV.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl, N. E. et al., *Proc. Nat'l Acad. Sci.*, 85, 4686 (1988) demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

The nucleotide sequence of HIV shows the presence of a pol gene in one open reading frame [Ratner, L. et al., *Nature*, 313, 277(1985)]. Amino acid sequence homology provides evidence that the pol sequence encodes reverse transcriptase, an endonuclease and an HIV protease [Toh, H. et al., *EMBO J.*, 4, 1267 (1985); Power, M. D. et al., *Science*, 231, 1567 (1986); Pearl, L. H. et al., *Nature*, 329, 351 (1987)]. Applicants demonstrate that the compounds of this invention are inhibitors of HIV protease.

BRIEF DESCRIPTION OF THE INVENTION

Compounds of Formula I, as herein defined, are disclosed. These compounds are useful in the inhibition of HIV protease, the prevention of infection by HIV, the treatment of infection by HIV and in the treatment of AIDS, either as compounds, pharmaceutically acceptable salts, pharmaceutical composition ingredients, whether or not in combination with other antivirals, immunomodulators, antibiotics or vaccines. Methods of treating AIDS, methods of preventing infection by HIV, and methods of treating infection by HIV are also disclosed.

DETAILED DESCRIPTION OF THE INVENTION AND PREFERRED EMBODIMENTS

This invention is concerned with compounds of Formula I, combinations thereof, or pharmaceutically acceptable salts thereof, in the inhibition of HIV protease, the prevention or treatment of infection by HIV and in the treatment of the resulting acquired immune deficiency syndrome (AIDS). Compounds of Formula I are defined as follows:

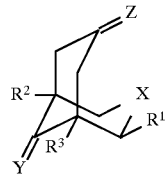

wherein

X is —O—, —NH—, —NR$^4$— or —S—;

Y is =O, or forms, with the carbon to which it is attached,

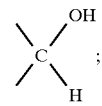

Z is =O, or forms, with the carbon to which it is attached,

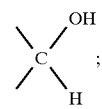

$R^1$ is
  a) H;
  b) $C_{1-4}$ alkyl;
  c) $C_{3-7}$ cycloalkyl;
  d) aryl, unsubstituted or substituted one or more times with hydroxy;
  e) $CH_2R^5$; or
  f) 5–7 membered heterocycle; and $R^2$ is
  a) $C_{1-4}$ alkyl;
  b) aryl, unsubstituted or substituted with aryl;
  c) $CH_2R^6$; or
  d) heterocycle; and $R^3$ is
  a) CH(OH)$R^7$; or
  b) CH(NH$_2$)$R^7$; and $R^4$ is
  a) $C_{1-4}$ alkyl;
  b) $C_{3-6}$ cycloalkyl;
  c) aryl unsubstituted or substituted with halo or with $C_{1-4}$ alkyl unsubstituted or substituted one or more times with hydroxy;
  d) $CH_2R^1$; or
  e) 5–7 membered heterocycle; and $R^5$ is
  a) $C_{1-4}$ alkyl; or
  b) aryl; and $R^6$ is
  a) $C_{1-4}$ alkyl;
  b) aryl unsubstituted or substituted with halo or with $C_{1-4}$ alkyl unsubstituted or substituted one or more times with hydroxy; or
  c) 5–7 membered heterocycle; and $R^7$ is
  a) H;
  b) $C_{1-4}$ alkyl;
  c) aryl unsubstituted or substituted with amino;
  d) $C_{1-3}$ alkylaryl unsubstituted or substituted with amino; or e) 5–7 membered heterocycle;
or pharmaceutically acceptable salt thereof.

One preferred embodiment is a compound of the formula

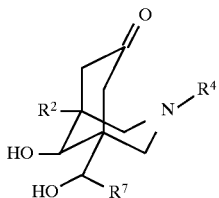

wherein
$R^2$ is $C_{1-4}$ alkylene-aryl; and
$R^4$ is $C_{1-4}$ alkyl, unsubstituted or substituted with aryl, $C_{3-6}$ cycloalkyl, or 5–7 membered heterocycle;
$R^7$ is H, benzyl unsubstituted or substituted with amino;
or pharmaceutically acceptable salt thereof.

Preferred compounds of this invention are shown below.
Compound A:

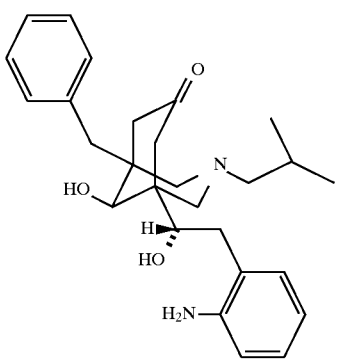

or pharmaceutically acceptable salts thereof; and
Compound B:

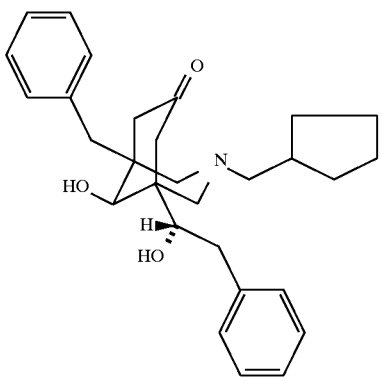

or pharmaceutically acceptable salts thereof.

The compounds of the present invention, may have asymmetric centers and occur as racemates, racemic mixtures and as individual diastereomers, or enantiomers with all isomeric forms being included in the present invention.

When any variable (e.g., aryl, heterocycle, $R^1$, $R^2$, X, Y, or Z, etc.) occurs more than one time in any constituent or in Formula I, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl).

As used herein, with exceptions as noted, "aryl" is intended to mean phenyl (Ph) or naphthyl.

The term heterocycle or heterocyclic, as used herein except where noted, represents a stable 5- to 7-membered mono- or bicyclic or stable 7- to 10-membered bicyclic heterocyclic ring system, any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl.

The pharmaceutically-acceptable salts of the compounds of Formula I (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Other pharmaceutically acceptable salts include the sulfate salt ethanolate and sulfate salts.

Schemes I and II for preparing the novel compounds of this invention are presented below. Tables I and II which follow the schemes illustrate the compounds that can be synthesized by Schemes I and II, but Schemes I and II are not limited by the compounds in the tables nor by any particular substituents employed in the schemes for illustrative purposes. The examples specifically illustrate the application of the following schemes to specific compounds.

Additional related information on synthetic background is contained in EPO 0337714.

One method for producing Formula I compounds is provided by Scheme I.

SCHEME I

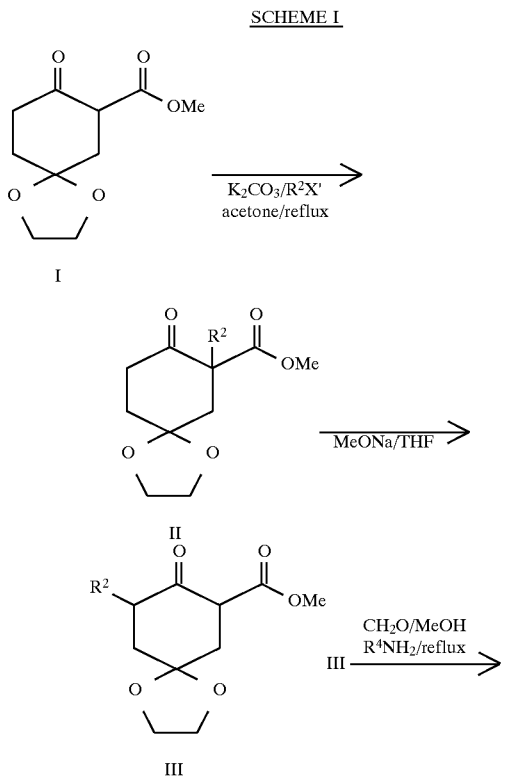

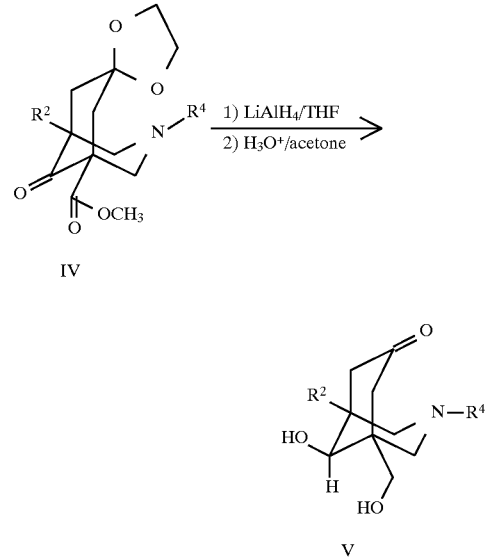

Alkylation of ester I by reaction with R²X' (wherein X' is halo) in base gives II. Reaction with MeONa rearranges II to afford III. Cyclization of R⁴NH₂ gives the azabicyclic (3.3.1) nonane core precursor IV which, after reduction and acid hydrolysis, provides V. Scheme I is illustrated as one embodiment in Example 1.

SCHEME II

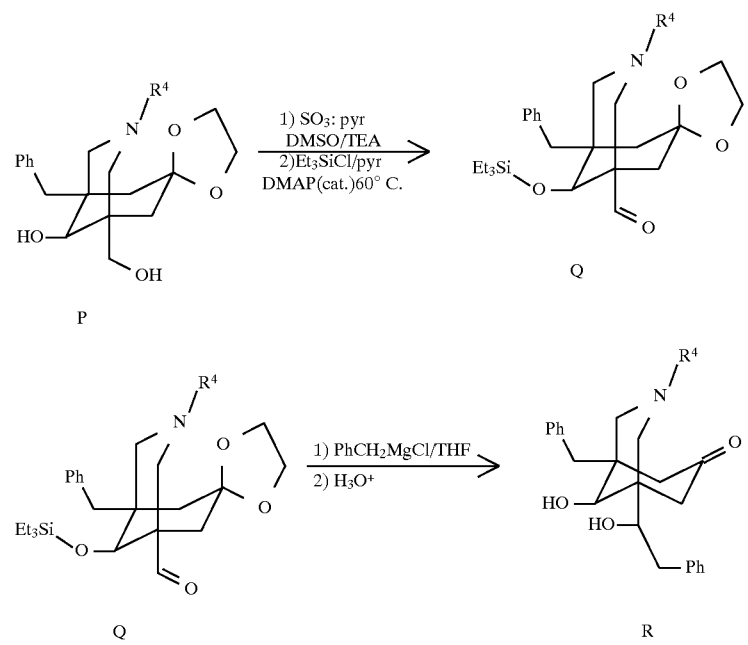

Scheme II outlines another general synthetic method. Alcohol oxidation by treatment of P with SO₃.pyridine complex in DMSO, followed by silylation, gives Q. Alkylation with the appropriate Grignard reagent, followed thereafter with acid treatment, affords R. Scheme II is also illustrated in one embodiment in Example 3.

The compounds of this invention are also illustrated by Tables I–II, which follow.

TABLE 1

[Structure: bicyclic ketone with $R^2$, HO, H, OH, and N–$R^4$ substituents]

| Compound | $R^4$ | $R^2$ | % inhibition | Enzyme concentration ($\mu$M) | IC$_{50}$ ($\mu$M) |
|---|---|---|---|---|---|
| 1 | CH₂CH=CH₂ (allyl) | CH=CH–Ph | 77 | 250 | |
| 2 | CH₂-cyclopropyl | CH₂Ph | 56 | 250 | |
| 3 | CH₂-C(CH₃)₃ (neopentyl) | CH₂Ph | 69 | 250 | |
| 4 | CH₂Ph | CH₂Ph | 82 | 250 | |
| 5 | CH₂CH(CH₃)₂ (isobutyl) | CH₂Ph | 63 | 250 | |
| 6 | CH₂CH(CH₃)₂ | CH₂-C₆H₄-Br | 71 | 250 | 244 |
| 7 | CH₂CH(CH₃)₂ | CH₂-C₆H₄-(2-OMe-C₆H₄) | 56 | 100 | |
| 8 | CH₂CH₂C(CH₃)₂- | CH₂-Ph | 68 | | |
| 9 | CH₂-cyclopentyl | CH₂-Ph | | 89 | |
| 10 | CH₂CH(CH₃)₂ | CH₂-C₆H₄-(furanyl) | 62 | 100 | |
| 11 | CH=C(CH₃)₂ | CH₂-C₆H₄-Br | 76 | 100 | 30 |
| 12 | C(CH₃)₃ | CH₂-naphthyl | 43 | 100 | |

TABLE 1-continued

[Structure: bicyclic ketone with R², HO, H, OH, CH₂OH, and N—R⁴ substituents]

| Compound | R⁴ | R² | % inhibition | Enzyme concentration (μM) | IC₅₀ (μM) |
|---|---|---|---|---|---|
| 13 | CH₂-CH(CH₂OH)-CH₂-CH(CH₃)₂ (S) | CH₂-phenyl | 75 | | 44 |
| 14 | CH₂-CH(CH₂OH)-CH₂-CH(CH₃)₂ (racemic) | CH₂-phenyl | 62 | | |

TABLE II

[Structure: bicyclic ketone with R², HO, HO, R⁷, and N—R⁴ substituents]

| Compound | R⁷ | R² | R⁴ | % inhibition | Enzyme concentration (μM) | IC₅₀ (μM) |
|---|---|---|---|---|---|---|
| 15 | n-Bu | CH₂-phenyl | isobutyl | 73 | 100 | 14 |
| 16 | CH₂-phenyl | CH₂-phenyl | isobutyl | 82 | (8.8) 50 | |
| 17 | 4-ethynyl-phenyl | CH₂-phenyl | CH₂-phenyl | 52 | 50 | |
| 18 | CH₂-phenyl | CH₂-phenyl | CH₂-phenyl | 63 | 50 | |

TABLE II-continued

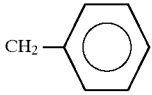

| Compound | R⁷ | R² | R⁴ | % inhibition | Enzyme concentration ($\mu$M) | IC$_{50}$ ($\mu$M) |
|---|---|---|---|---|---|---|
| 19 | 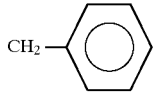 |  |  | 44 | 50 | |
| 20 | 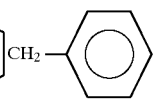 | 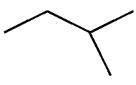 | 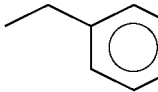 | 93 | 100 | 1.6 |
| 21 | 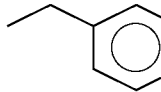 | 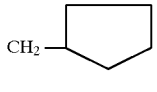 | 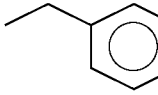 | 80 | 25 | 1.8 |
| 22 | 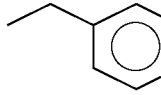 | 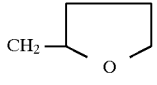 | 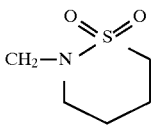 | 84 | 100 | 10.4 |
| 23 | 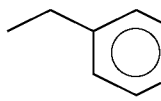 | 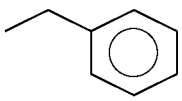 |  | 69 | 100 | 29 |

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV protease, e.g., by competitive inhibition. Thus the compounds of this invention are commercial products to be sold for these purposes.

The compounds of the present invention are useful in the inhibition of HIV protease the prevention or treatment of infection by the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

For these purposes, the compounds of the present invention may be administered orally, parenterally (including subcutaneous injections, intravenous, intramuscular, intrastemal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically effective amount of a compound of the present invention, or a pharmaceutically acceptable salt thereof.

These pharmaceutical compositions may be in the form of orally-administrable suspensions or tablets; nasal sprays; sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

Dosage levels of the order of 0.02 to 5.0 or 10.0 grams-per-day are useful in the treatment or prevention of the above-indicated conditions, with oral doses two-to-five times higher. For example, infection by HIV is effectively treated by the administration of from 1.0 to 50 milligrams of the compound per kilogram of body weight from one to four times per day. In one preferred regimen, dosages of 100–400 mg every six hours are administered orally to each patient. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention is also directed to combinations of the HIV protease inhibitory compounds with one or more agents useful in the treatment of AIDS. For example, the compounds of this invention may be effectively administered, whether at periods of pre-exposure and/or post-exposure, in combination with effective amounts of the AIDS antivirals, immunomodulators, anti-infectives, or vaccines known to those of ordinary skill in the art.

TABLE C

| Drug Name | Manufacturer | Indication |
|---|---|---|
| ANTIVIRALS | | |
| AL-721 | Ethigen (Los Angeles, CA) | ARC, PGL HIV positive, AIDS |
| Recombinant Human Interferon Beta | Triton Biosciences (Almeda, CA) | AIDS, Kaposi's sarcoma, ARC |
| Acemannan | Carrington Labs (Irving, TX) | ARC (See also immunomodulators) |
| Cytovene Ganciclovir | Syntex (Palo Alto, CA) | sight threatening CMV peripheral CMV retinitis |
| d4T Didehydrodeoxy-thymidine | Bristol-Myers (New York, NY) | AIDS, ARC |
| ddI Dideoxyinosine | Bristol-Myers (New York, NY) | AIDS, ARC |
| EL10 | Elan Corp, PLC (Gainesville, GA) | HIV infection (See also immunomodulators) |
| Trisodium Phosphonoformate | Astra Pharm. Products, Inc (Westborough, MA) | CMV retinitis, HIV infection, other CMV infections |
| Dideoxycytidine; ddC | Hoffman-La Roche (Nutley, NJ) | AIDS, ARC |

TABLE C-continued

| Drug Name | Manufacturer | Indication |
|---|---|---|
| Novapren | Novaferon Labs, Inc. (Akron, OH) Diapren, Inc. (Roseville, MN, marketer) | HIV inhibitor |
| Peptide T Octapeptide Sequence | Peninsula Labs (Belmont, CA) | AIDS |
| Zidovudine; AZT | Burroughs Wellcome (Rsch. Triangle Park, NC) | AIDS, adv, ARC pediatric AIDS, Kaposi's sarcoma, asymptomatic HIV infection, less severe HIV disease, neurological involvement, in combination with other therapies. |
| Ansamycin LM 427 | Adria Laboratories (Dublin, OH) Erbamont (Stamford, CT) | ARC |
| Dextran Sulfate | Ueno Fine Chem. Ind. Ltd. (Osaka, Japan) | AIDS, ARC, HW positive asymptomatic |
| Virazole Ribavirin | Viratek/ICN (Costa Mesa, CA) | asymptomatic HIV positive, LAS, ARC |
| Alpha Interferon | Burroughs Wellcome (Rsch. Triangle Park, NC) | Kaposi's sarcoma, HIV in combination w/Retrovir |
| Acyclovir | Burroughs Wellcome | AIDS, ARC, asymptomatic HIV positive, in combination with AZT. |
| Antibody which neutralizes pH labile alpha aberrant Interferon in an immuno-adsorption column | Advanced Biotherapy Concepts (Rockville, MD) | AIDS, ARC |
| L-743,726 | Merck (Rahway, NJ) | AIDS, ARC, asymptomatic HIV positive, also in combination with AZT. |
| IMMUNO-MODULATORS | | |
| AS-101 | Wyeth-Ayerst Labs. (Philadelphia, PA) | AIDS |
| Bropirimine | Upjohn (Kalamazoo, MI) | advanced AIDS |
| Acemannan | Carrington Labs, Inc. (Irving, TX) | AIDS, ARC (See also anti-virals) |
| CL246,738 | American Cyanamid (Pearl River, NY) Lederle Labs (Wayne, NJ) | AIDS, Kaposi's sarcoma |
| EL10 | Elan Corp, PLC (Gainesville, GA) | HIV infection (See also anti-virals) |
| Gamma Interferon | Genentech (S. San Francisco, CA) | ARC, in combination w/TNF (tumor necrosis factor) |
| Granulocyte Macrophage Colony Stimulating Factor | Genetics Institute (Cambridge, MA) Sandoz (East Hanover, NJ) | AIDS |
| Granulocyte Macrophage Colony Stimulating Factor | Hoeschst-Roussel (Sommerville, NJ) Immunex (Seattle, WA) | AIDS |
| Granulocyte Macrophage Colony Stimulating Factor | Schering-Plough (Madison, NJ) | AIDS AIDS, in combination w/AZT |
| HIV Core Particle Immunostimulant | Rorer (Ft. Washington, PA) | seropositive HIV |

TABLE C-continued

| Drug Name | Manufacturer | Indication |
|---|---|---|
| IL-2 Interleukin-2 | Cetus (Emeryville, CA) | AIDS, in combination w/AZT |
| IL-2 Interleukin-2 | Hoffman-La Roche (Nutley, NJ) Immunex | AIDS, ARC, HIV, in combination w/AZT |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute (Miami, FL) | AIDS, ARC |
| Alpha-2 Interferon | Schering Plough (Madison, NJ) | Kaposi's sarcoma w/AZT: AIDS |
| Methionine- Enkephalin | TNI Pharmaceutical (Chicago, IL) | AIDS, ARC |
| MTP-PE Muramyl- Tripeptide | Ciba-Geigy Corp. (Summit, NJ) | Kaposi's sarcoma |
| Granulocyte Colony Stimulating Factor | Amgen (Thousand Oaks, CA) | AIDS, in combination w/AZT |
| rCD4 Recombinant Soluble Human CD4 | Genentech (S. San Francisco, CA) | AIDS, ARC |
| rCD4-IgG hybrids | | AIDS, ARC |
| Recombinant Soluble Human CD4 | Biogen (Cambridge, MA) | AIDS, ARC |
| Interferon Alfa 2a | Hoffman-La Roche (Nutley, NJ) | Kaposi's sarcoma AIDS, ARC, in combination w/AZT |
| SK&F106528 Soluble T4 | Smith, Kline & French Laboratories (Philadelphia, PA) | HIV infection |
| Thymopentin | Immunobiology Research Institute (Annandale, NJ) | HIV infection |
| Tumor Necrosis Factor; TNF | Genentech (S. San Francisco, CA) | ARC, in combination w/gamma Interferon |
| ANTI-INFECTIVES | | |
| Clindamycin with Primaquine | Upjohn (Kalamazoo, MI) | PCP |
| Fluconazole | Pfizer (New York, NY) | cryptococcal meningitis, candidiasis prevention of |
| Pastille Nystatin Pastille | Squibb Corp. (Princeton, NJ) | oral candidiasis |
| Ornidyl Eflornithine | Merrell Dow (Cincinnati, OH) | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome (Rsch. Triangle Park, NC) | PCP treatment |
| Pentamidine isethionate for inhalation | Fisons Corporation (Bedford, MA) | PCP prophylaxis |
| Spiramycin | Rhone-Poulenc Pharmaceuticals (Princeton, NJ) | cryptosporidial diarrhea |
| Intraconazole- R51211 | Janssen Pharm. (Piscataway, NJ) | histoplasmosis; cryptococcal meningitis |
| Trimetrexate | Warner-Lambert | PCP |
| OTHER | | |
| Recombinant Human Erythropoietin | Ortho Pharm. Corp. (Raritan, NJ) | severe anemia assoc. with AZT therapy |
| Megestrol Acetate | Bristol-Myers (New York, NY) | treatment of anorexia assoc. |

TABLE C-continued

| Drug Name | Manufacturer | Indication |
|---|---|---|
| Total Enteral Nutrition | Norwich Eaton Pharmaceuticals (Norwich, NY) | w/AIDS diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Certain compounds of Table S are the following: L-743, 726 is (−) 6-chloro-4(S)-cyclopropylethynyl-4(S)-trifluoromethyl-1,4-dihydro-2H-3,1-benzoxazin-2-one, and is synthesized according to EP 0 582,455.

The synthesis of ddC, ddI and AZT are also described in EPO 484071.

Preferred combinations are simultaneous or alternating treatments of an inhibitor of HIV protease and a non-nucleoside inhibitor of HIV reverse transcriptase. An optional third component in the combination is a nucleoside inhibitor of HIV reverse transcriptase, such as AZT, ddC or ddI. A preferred inhibitor of HIV protease is L-735,524 (Compound J), disclosed and synthesized according to U.S. Pat. No. 5,413,999. Preferred non-nucleoside inhibitors of HIV reverse transcriptase include L-743,726. These combinations may have synergistic effects on limiting the spread of HIV. Preferred combinations include the following (1) L-735,524, with L-743,726, and, optionally, AZT or ddI or ddC; (2) L-735,524, and any of AZT or ddI or ddC.

Assay for Inhibition of Microbial Expressed HIV Protease

Inhibition studies of the reaction of the protease expressed in *Eschericia coli* with a peptide substrate [Val-Ser-Gln-Asn-(betanapthyl)Ala-Pro-Ile-Val, 0.5 mg/mL at the time the reaction is initiated] were in 50 mM Na acetate, pH 5.5, at 30° C. for 1 hour. Various concentrations of inhibitor in 1.0 μl DMSO were added to 25 μl of the peptide solution in water. The reaction is initiated by the addition of 15 μl of 0.33 nM protease (0.11 ng) in a solution of 0.133M Na acetate pH 5.5 and 0.1% bovine serum albumin. The reaction was quenched with 160 μl of 5% phosphoric acid. Products of the reaction were separated by HPLC (VYDAC wide pore 5 cm C-18 reverse phase, acetonitrile gradient, 0.1% phosphoric acid). The extent of inhibition of the reaction was determined from the peak heights of the products. HPLC of the products, independently synthesized, proved quantitation standards and confirmation of the product composition. Tables I and II provide results for a variety of compounds.

EXAMPLE 1

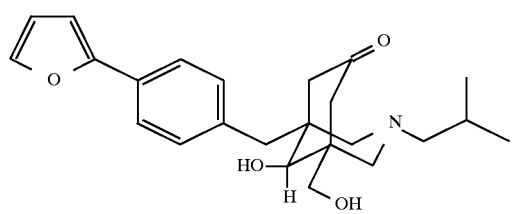

5(RS)-((4')-2"-furanyl)methylpheny-9(RS)-hydroxy-1(RS)-hydroxy-methyl-3-(2'-methylpropyl-3-azabicyclo[3.3.1] nonan-7-one (Compound 10, Table 1)

Step 1: Compound A

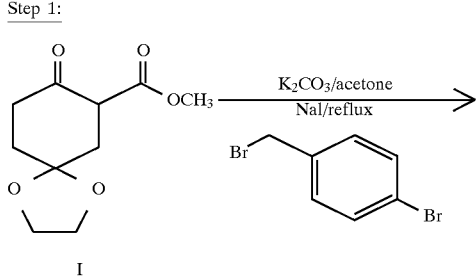

To a solution of 2-carbomethoxy-4-ethylenedioxycyclohexanone I, (3.0 g, 14.0 mmol, Fuchs, P. L. et al., *Syn. Comm*, 13(3), 243, 1983) in 100 mL, of acetone was added 4-bromobenzyl bromide (3.67 g, 14.7 mmol), $K_2CO_3$ (9.69 g, 70.1 mmol) and NaI (210 mg, 1.4 mmol). The heterogenous reaction was heated at reflux for 16 h. The reaction mixture was cooled and filtered through Celite. The filtrate was diluted with 250 mL of $Et_2O$ and the organics were washed with water (2×20 mL) t hen brine (50 mL) and dried over $MgSO_4$. Evaporation of the solvent and flash chromatography ($SiO_2$; 4:1 Hexane/EtOAc) gave 4.8 g (89%) of A.

$^1$H NMR (CDCl$_3$) δ 7.40 (d, J=7.8 Hz, 2H), 7.05 (d, J=7.8 Hz, 2H), 3.98 (m, 5H), 3.60 (s, 3H), 3.00 (m, 3H), 2.50 (m, 2H), 1.95 (m, 2H).

Step 2: Compound B

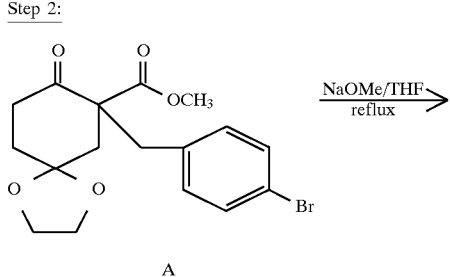

To a slurry of NaH (375 mg, 15.6 mmol) in THF (15 mL) at 0° C. was added MeOH (0.76 mL, 30.7 mmol). After stirring for 5 min, keto ester A (4.8 g, 12.5 mmol) in THF (30 mL) was added dropwise and the solution was warmed to room temperature and stirred for 16 h. The reaction mixture was diluted with 50 mL of EtOAc, then excess NaOMe was quenched with 10 mL of saturated NH$_4$Cl. The organic phase was separated, washed with brine and dried over MgSO$_4$. Evaporation of the solvent and flash chromatography (SiO$_2$; 4;1 Hexane/EtOAc) gave 4.5 g (94%) of B.

$^1$H NMR (400 MHz, CDCl$_3$) δ 12.6 (s, 1H), 7.40 (d, J=7.8 Hz, 2H), 7.05 (d, J=7.8 Hz, 2H), 3.98 (m, 4H), 3.75 (s, 3H), 3.25 (m, 1H), 2.99 (m, 1H), 2.78 (m, 1H), 2.4–1.8 (m, 4H).

Step 3: Compound C

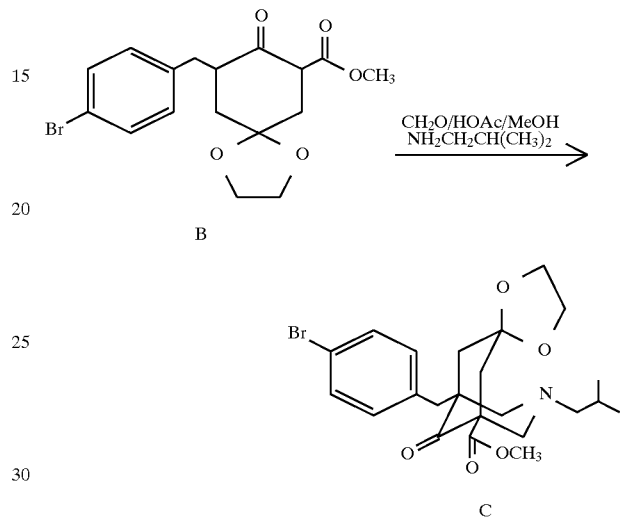

To a solution of keto ester (2.9 g, 7.57 (mmol) B in MeOH (45 mL) and an aqueous solution of formaldehyde (37%, 5.6 mL, 75.7 mmol) was added isobutyl amine (0.9 mL, 9.1 mmol) and HOAc (0.52 mL, 9.1 mmol). The whole was heated at reflux for 16 h. The reaction was cooled to room temperature and the solvent was removed. The residue was dissolved in EtOAc (100 mL) and the resulting solution was washed with sat'd NaHCO$_3$ (2×20 mL), water (2×20 mL) then brine (50 mL) and dried over MgSO$_4$. Evaporation of the solvent and flash chromatography (SiO$_2$ gradient; 4:1, 2:1, 1:1 Hexane/EtOAc gave 2.5 g (70%) of C. m.p. 142°–144° C.

$^1$H NMR (400 MHz, CDCl$_3$) δ 7.40 (d, J=7.8 Hz, 2H), 7.05 (d, J=7.8 Hz, 2H), 3.98 (m, 4H), 3.80 (s, 3H), 3.65 (m, 1H), 3.00 (dd, J=2.5, 11.0 Hz, 1H), 2.85 (d, J=14.1 Hz, 1H), 2.70 (m, 4H), 2.56 (d, J=13.2 Hz, 1H), 2.40 (d, J=13.2 Hz, 1H), 2.20 (m, 3H), 1.70 (m, 1H), 0.90 m, 6H).

Step 4: Compound D

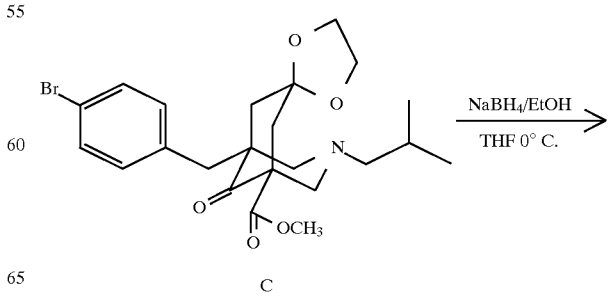

-continued

Step 4: Compound D

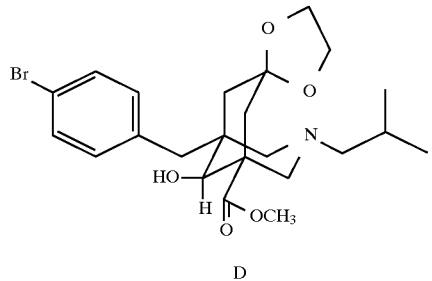

D

To a solution of ketone (1.8 g, 3.75 mml) C in 18 mL of 1:1:1 EtOH, CH$_2$Cl$_2$ and H$_2$O at 0° C. was added NaBH$_4$ (142 mg, 3.75 mmol). The solution was stirred for 30 min, then excess NaBH$_4$ was quenched with 5 mL of acetone. The solution was diluted with EtOAc and washed with water (4×10 mL) then brine (10 mL). Evaporation of the solvent and column chromatography (SiO$_2$; 65:35 Hexane/EtOAc) gave 964 mg (53%) of D.

$^1$H NMR (400 MHz, CDCl$_3$) δ 7.40 (d, J=7.8 Hz, 2H), 7.05 (d, J=7.8 Hz, 2H), 4.50 (d, J=11 Hz, 1H), 4.20–3.90 (m, 4H), 3.75 (s, 3H), 3.40 (d, J=11.2 Hz, 1H), 2.90 (d, J=13.5 Hz, 1H), 2.80 (d, J=12.2 Hz, 1H), 2.60 (m, 2H), 2.40 (d, J=10.6 Hz, 1H), 2.20 (d, J=10.4 Hz, 1H), 2.00–1.80 (m, 5H), 1.70 (m, 1H), 0.90 m, 6H).

Step 5: Compound E

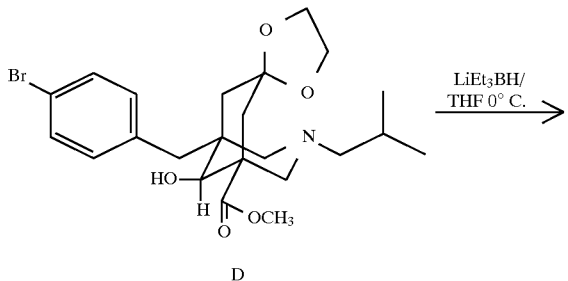

LiEt$_3$BH/
THF 0° C.

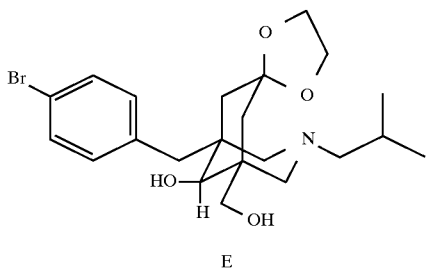

E

To a solution of ester (964 mg, 2.0 mmol) of D in THF (40 mL) at 0° C. was added LiEt$_3$BH (6.09 mL, 6.0 mmol). The solution was warmed to room temperature and stirred for 4 hours. Excess LiEt$_3$BH was quenched with 5 mL of saturated NaHCO$_3$. The solution was diluted with Et$_2$O (50 mL) and washed with saturated NaHCO$_3$ (3×10 mL), water (4×10 mL) and brine (10 mL). Evaporation of the solvent left 800 mg (88%) of crude diol E which was used directly in the next step without purification. m.p. 136°–138° C.

$^1$H NMR (400 MHz, CDCl$_3$) δ 7.39 (d, J=8.2 Hz, 2H), 7.13 (d, J=8.2 Hz, 2H), 4.74 (d, J=11.9 Hz, 1H), 4.05 (m, 4H), 3.57 (d, J=10.8 Hz, 1H), 3.39 (t, J=10.82 Hz, 1H), 3.-6 (d, J=11.9 Hz, 1H), 2.96 (d, J =13.4 Hz, 2H), 2.50 (d, J=13.4 Hz, 1H), 2.34 (d, J=10.6 Hz, 1H), 2.27 (d, J=10.6 Hz, 1H), 2.09 (t, J=11.7 Hz, 2H), 1.95 (d, J=17.3 Hz, 2H), 1.85 (d, J=14.3 Hz, 1H), 1.77 (m, 1H), 1.63 (t, J=11.1 Hz, 3H), 0.90 (d, J=12.4 Hz, 6H).

Step 6: Compound F (L-770,274)

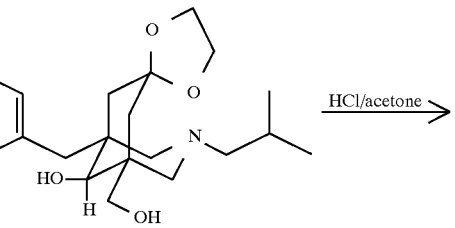

HCl/acetone →

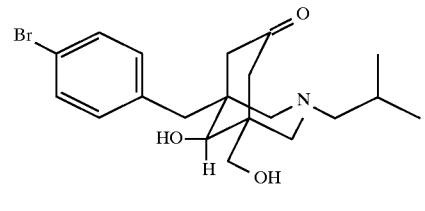

F

To a solution of ketal (453 mg, 1.0 mmol) E in acetone (8 mL) at 0° C. was added 8 mL of 50% HCl in water. The solution was heated at reflux for 16 h, then cooled to 0° C. Saturated NaHCO$_3$ solution was added to quench excess HCl. The solution was then washed with EtOAc (3×10 mL) and the combined organic extracts were dried over MgSO$_4$. Evaporation of the solvent and trituration of the resulting white solid with Et$_2$O gave 300 mg (73%) of F. m.p. 155°–156° C.

$^1$H NMR (400 MHz, CDCl$_3$) δ 7.40 (d, J=7.8 Hz, 2H), 7.05 (d, J=7.8 Hz, 2H), 3.95 (s, 1H), 3.65 (dd, J=4.4, 10.4 Hz, 1H), 3.49 (s, 1H), 3.45 (dd, J=4.6, 10.4 Hz, 1H), 2.80 (m, 2H), 2.60 (d, J=14.2 Hz, 2H), 2.52 (t, J=3.7 Hz, 1H), 2.43 (d, J=11.4 Hz, 1H), 2.35 (d, J=11.1 Hz, 1H), 2.00 (m 4H), 1.83 (d, J=11.2 Hz, 1H), 1.69 (d, J=11.2 Hz, 1H), 1.60 (m, 1H), 0.76 (m, 6H). Anal calc'd for C$_{20}$H$_{28}$NO$_3$Br: C, 58.54;H, 6.88;N, 3.41. Found: C, 58.91;H, 6.88;N, 3.51.

Step 7: Compound 10, Table I

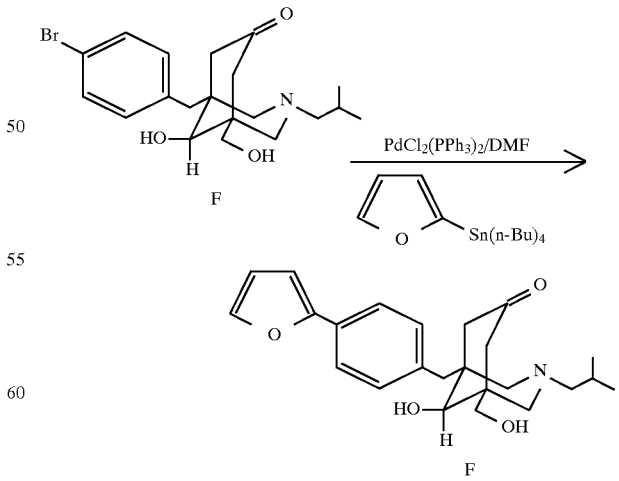

To a solution of the aryl bromide (41 mg, 0.10 mmol) in DMF (0.4 mL) was added 2-(tri-n-butylstannyl) furan (53.5 mg, 0.15 mmol) and PdCl$_2$(PPh$_3$)$_2$ (1.5 mg, 0.0020 mmol).

The resulting yellow-brown solution was stirred at 95° C. for 4 h. The reaction mixture was cooled, diluted with ether and filtered through Celite. The filtrate was washed with water (7×2 mL), brine (2 mL) and dried over MgSO$_4$. The yellow oil was subjected to flash chromatography (SiO$_2$; 95:5:0.5 CHCl$_3$/IPA/NH$_4$OH) to afford 25 mg (63%) of the title compound as a foam.

$^1$H NMR (400 MHz, CDCl$_3$) δ 7.60 (d, J=7.8 Hz, 2H), 7.45 (d, J=0.8 Hz, 1H), 7.21 (d, J=7.8 Hz, 2H), 6.62 (d, J=4.2 Hz, 1H), 6.44 (dd, J=4.2, 0.8 Hz, 1H), 3.81 (s, 1H), 3.63 (m, 3H), 3.50 (m, 2H), 2.85 (m, 2H), 2.60 (m, 4H), 2.45 (d, J=14 Hz, 1H), 2.35 (d, J=14 Hz, 1H), 1.8–2.1 (m, 6H), 1.7 (d, J=14 Hz, 1H), 1.6 (m, 2H), 0.77 (d, J=8 Hz, 6H). Anal calc'd for C$_{24}$H$_{31}$NO$_4$.0.8 H$_2$O: C, 69.97; H, 7.98; N, 3.40. Found: C, 69.95; H, 7.70; N, 3.52.

EXAMPLE 2
5(RS)-methylphenyl-9(RS)-hydroxy-1(RS)-((1'-hydroxy)-2'-phenyl)-ethyl-3-(2"-methyl)propyl-3-azabicyclo[3.3.1]nonan-7-one (Compound 16), Table II

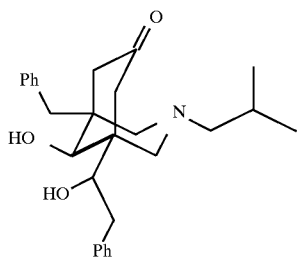

Step 1: Compound G

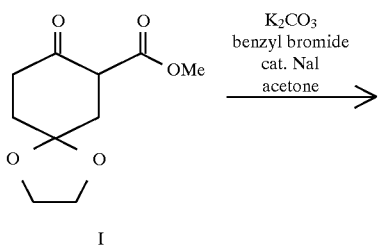

A mixture of I (12.0 g, 56.0 mmnol), benzyl bromide (10.1 g, 7.0 mL, 58.8 mmol), potassium carbonate (48.4 g, 350 mmol), and sodium iodide (250 mg, 1.7 mmol) in acetone (200 mL) was heated at reflux for 16 h. The heterogeneous mixture was then poured into water (150 mL). The aqueous mixture was extracted with ethyl acetate (2×200 ml). The combined organic layers were dried over Na$_2$SO$_4$ and concentrated to give G as a colorless oil (18.7 g). Rƒ=0.16 (20% EtOAc/Hexane)] which was used without further purification.

$^1$H NMR (400 MHz, CDCl$_3$) δ 7.17–7.26 (m, 5H), 3.91–4.03 (m, 4H), 3.63 (s, 3H), 3.15 (d, 1H, J=13.6 Hz), 3.03 (d, 1H, J=13.6 Hz), 2.97 (ddd, 1H, J=15.0, 8.1, 12.3 Hz), 2.58 (dd, 1H, J=14.1, 2.9 Hz), 2.49 (ddd, 1H, J=15.0, 4.8, 3.7 Hz), 1.91–1.95 (m, 2H), 1.78 (d, 1H, J=13.9 Hz).

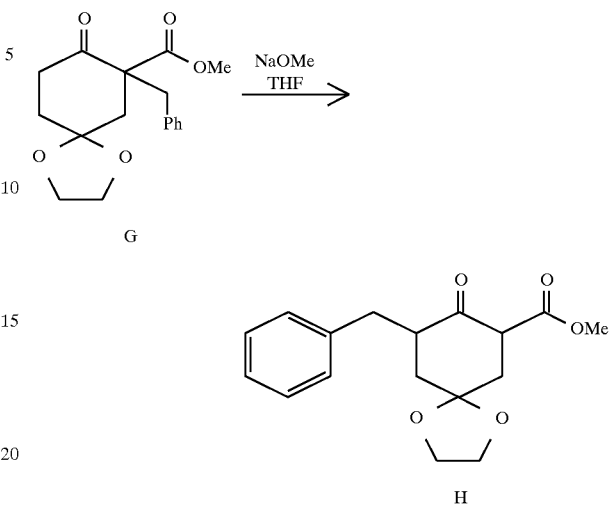

Step 2: Compound H

Sodium hydride (2.40 g, 61 mmol, 60 wt % in mineral oil) was washed with hexane to remove mineral oil and then was suspended in tetrahydrofuran (80 mL) at 0° C. Anhydrous methanol (2.15 g, 2.72 mL, 67.1 mmol) was added dropwise over 3 min., followed by warming to 23° C. and stirred for 30 min. The resulting suspension was cooled to 0° C. and G was added via dropping funnel in tetrahydrofuran (40 mL) over 30 min. The reaction mixture was allowed to warm to 23° C. over 1 h and then was stirred at that temperature for 16 h. Aqueous acetic acid (10%, 10 mL) was carefully added and the mixture was poured into saturated NaHCO$_3$ (100 mL), washed with EtOAc (2×150 mL), dried (Na$_2$SO$_4$) and concentrated to give a brown oil. Recrystallization from MeOH afforded H as white prisms (11.2 g). The mother liquor was concentrated and purified by flash chromatography (20% EtOAc/Hexane) to give a colorless oil which was further purified by recrystallization from Et$_2$O to give H as white prisms (11.4 g overall, 67% yield for two steps), Rƒ=0.32 (30% EtOAc/Hexane), mp =110°–115° C.

$^1$H NMR (CDCl$_3$) δ 7.13–7.29 (m, 5H), 3.90–4.00 (m, 4H), 3.81 (dd, 1H, J=13.9, 5.7 Hz), 3.77 (s, 3H), 3.22 (dd, 1H, J=14.1, 5.0 Hz), 2.97–3.05 (m, 1H), 2.45 (dd, 1H, J=14.1, 8.6 Hz), 2.35 (t, 1H, J=13.6 Hz), 2.18 (ddd, 1H, J=13.4, 5.7, 3.8 Hz), 1.98 (ddd, 1H, J=13.2, 5.9, 3.8 Hz), 1.76 (t, 1H, J=13.4 Hz).

Step 3: Compound I

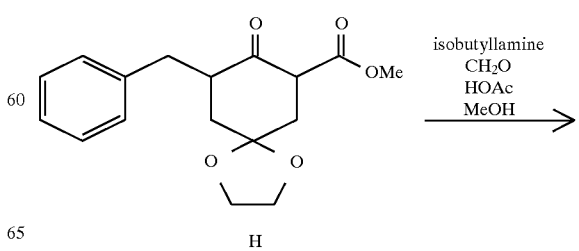

Step 3: Compound I

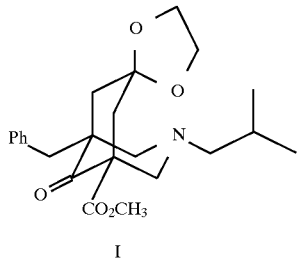

I

Isobutylamine (4.07 mL, 40.9 mmol), glacial acetic acid (2.28 mL, 39.8 mmol), aqueous formaldehyde (37%, 25.0 mL, 373 mmol), and 3 (10.38 g, 34.1 mmol) were heated at reflux in MeOH (200 mL) for 48 h. The reaction was then concentrated, diluted with EtOAc (125 mL), and poured into saturated NaHCO$_3$ (100 mL). The biphasic system was partitioned and the aqueous layer was washed with additional EtOAc (2×100 mL). The combined organics were dried (Na$_2$SO$_4$), concentrated, eluting with Et$_2$O (50 mL), and then filtered through silica gel washing with Et$_2$O (500 mL). The filtrate was concentrated to give 4 as a colorless oil [13.2 g, 96%, R$f$=0.27 (25% EtOAc/Hexane)]. This material was used without further purification.

$^1$H NMR (CDCl$_3$) δ 7.15–7.29 (m, 5H), 3.87–4.03 (m, 4H), 3.80 (s, 3H), 3.02 (dd, 1H, J=11.0, 3.1 Hz), 2.90 (d, 1H, J=13.9 Hz), 2.87 (d, 1H, J=14.1 Hz), 2.75 (d, 2H, J=11.0 Hz), 2.68 (dd, 1H, J=13.2, 3.5 Hz), 2.54 (d, 1H, J=13.0 Hz), 2.38 (d, 1H, J=13.2 Hz), 2.14–2.26 (m, 3H), 2.11 (dd, 1H, J=13.2, 3.5 ), 1.57–1.74 (m, 1H), 0.91 (d, 3H, J=6.6 Hz), 0.89 (d, 3H, J=6.6 Hz).

Step 4: Compound J

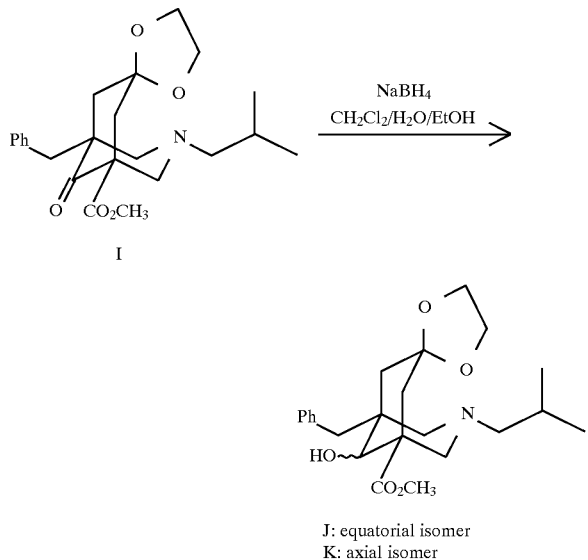

J: equatorial isomer
K: axial isomer

Ethanol was added to a suspension of I in dichloromethane:water:ethanol (200 mL, 1:2:1) until the solution became homogeneous. Sodium borohydride was added in one gram portions until TLC indicated that I had been consumed (7×1.0 g). The reaction mixture was cooled to 0° C. and acetone was slowly added until it no longer provoked gas evolution. The resulting mixture was then poured into saturated NaCl (150 mL) and washed with EtOAc (2×250 mL). The organic layer was dried (Na$_2$SO$_4$), concentrated, and purified by flash chromatography (30% EtOAc/Hexane) to give a mixture of J and K as a colorless oil (9.49 g, 72% yield), R$f$=0.23 (30% EtOAc/Hexane).

Compound J: $^1$H NMR (400 MHz, CDCl$_3$) δ 7.22–7.30 (m, 5H), 4.55 (d, 1H, J=11.2 Hz), 3.95–4.15 (m, 4H), 3.73 (s, 3H), 3.47 (d, 1H, J=11.3 Hz), 2.96 (d, 1H, J=13.4 Hz), 2.83 (dd, 1H, J=14.6, 2.1 Hz), 2.68 (d, 1H, J=13.4 Hz), 2.53 (dd, 1H, J=10.6, 2.1 Hz), 2.42 (dd, 1H, J=10.8, 2.2 Hz), 2.19 (d, 1H, J=10.4 Hz), 1.91–2.05 (m, 5H), 1.85 (d, 1H, J=10.7 Hz), 1.58–1.67 (m, 1H), 0.85 (t, 6H, J=7.4 Hz).

Compound K: $^1$H NMR (400 MHz, CDCl$_3$) δ 7.19–7.29 (m, 5H), 4.24 (s, 1H), 3.70–4.08 (m, 4H), 3.70 (s, 3H), 2.89 (d, 1H, J=13.2 Hz), 2.84 (d, 1H, J=10.0 Hz), 2.62 (d, 1H, J=10.8 Hz), 2.49 (d, 1H, J=13.4 Hz), 2.46 (d, 1H, J=11.9 Hz), 2.26 (d, 1H, J=10.8 Hz), 2.20 (d, 1H, J =14.1 Hz), 2.14 (d, 2H, J=7.3 Hz), 1.96 (d, 1H, J=14.5 Hz), 1.90 (d, 1H, J=14.0 Hz), 1.79 (d, 1H, J=14.1 Hz), 1.76–1.81 (m, 1H), 0.89 (d, 3H, J=3.9 Hz), 0.88 (d, 3H, J=4.0 Hz).

Step Compound L:

J + K $\xrightarrow{\text{TESCl, pyridine, cat. DMAP}}$

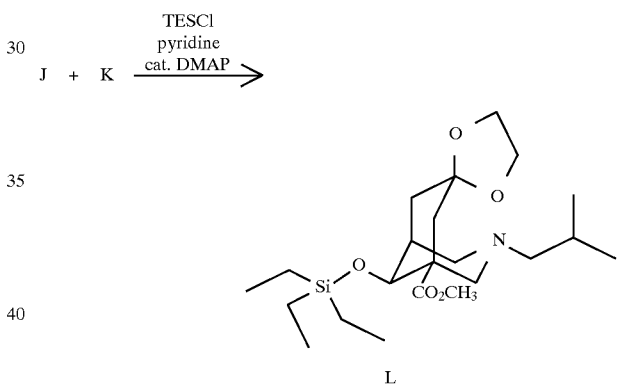

L

A mixture of J and K (2.16 g, 5.3 mmol, 1:1) in pyridine (40 mL) at 0° C. was treated with chlorotriethylsilane (4.03 g, 4.48 mL, 26.7 mmol). 4-Dimethylaminopyridine (2 mg) was added and the reaction mixture was heated at 60° C. for 4 h. The reaction mixture was then concentrated, and the residue was partitioned between Et$_2$O (100 mL) and saturated NaHCO$_3$ (100 mL). The organic layer was washed with saturated NaCl solution, dried (Na$_2$SO$_4$), and concentrated. The resulting oil was purified by flash chromatography (5% EtOAc/Hexane) to give L as a colorless oil (1.14 g, 41% yield of desired isomer), R$f$=0.33 (10% EtOAc/Hexane).

$^1$H NMR (400 MHz, CDCl$_3$) δ 7.14–7.31 (m, 5H), 4.04 (s, 1H), 3.76–3.83 (m, 4H), 3.71 (s, 3H), 2.83 (dd, 1H, J=11.3, 1.5 Hz), 2.78 (s, 2H), 2.62 (dd, 1H, J=11.6, 1.5 Hz), 2.40 (dd, 1H, J=11.8, 3.3 Hz), 2.08 (dd, 2H, J=7.3, 1.5 Hz), 2.00 (d, 2H, J=11.6 Hz), 1.88 (d, 1H, J=11.6 Hz), 1.82 (dd, 1H, J=11.5,3.4 Hz), 1.71 (d, 1H, J=11.4 Hz), 1.65–1.70 (m, 1H), 0.97 (t, 9H, J=8.0 Hz), 0.83 (d, 3H, J=7.2 Hz), 0.85 (d, 3H, J=6.7 Hz), 0.63 (q, 6H, J=7.9 Hz).

Compound M

Step 6:

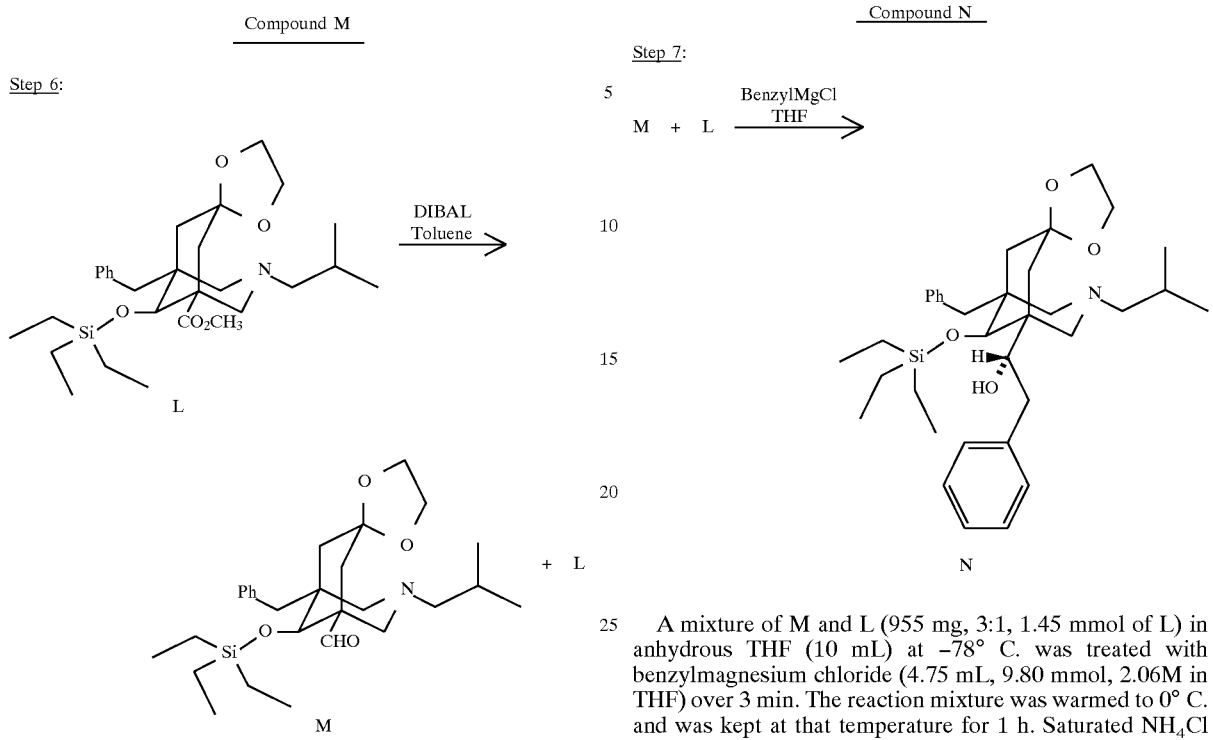

Diisobutylaluminum hydride (1.0M in toluene, 2.91 mL, 2.91 mmol) was cooled to −78° C. and added via cannula to a solution of L (753 mg, 1.45 mmol) in toluene (10 mL) at −78° C. The reaction mixture was stirred for 20 min and then acetone (5 mL) at −78° C. was added via cannula to destroy excess reagent. The mixture was allowed to warm to 23° C., poured into saturated sodium potassium tartrate (100 mL), and the resulting suspension was washed with EtOAc (2×100 mL). The organic layer was dried (Na$_2$SO$_4$) and concentrated to give a mixture of L and M as a colorless oil which was azeotropically dried with toluene (2×40 mL) and used without further purification (720 mg, 3:1 mixture of M:L, 75% yield of M), Rƒ=0.41 (50% EtOAc/Hexane)].

$^1$H NMR (400 MHz, CDCl$_3$) δ 9.66 (s, 1H), 7.13–7.32 (m, 5H), 3.71–3.82 (m, 5H), 2.78 (d, 2H, J=3.4 Hz), 2.74 (dd, 1H, J=11.8, 2.0 Hz), 2.66 (dd, 1H, J=11.8, 2.0 Hz), 2.21 (dd, 1H, J=11.9, 2.6 Hz), 2.10 (dd, 2H, J=7.5, 1.6 Hz), 1.93 (d, 1H, J=1.8 Hz), 1.92 (d, 1H, J=11.9 Hz), 1.83–1.87 (m, 3H), 1.65–1.73 (m, 1H), 0.97 (t, 9H, J=8.0 Hz), 0.85 (d, 3H, J=6.7 Hz), 0.83 (d, 3H, J=7.2 Hz), 0.63 (q, 6H, J=7.9 Hz).

Compound N

Step 7:

A mixture of M and L (955 mg, 3:1, 1.45 mmol of L) in anhydrous THF (10 mL) at −78° C. was treated with benzylmagnesium chloride (4.75 mL, 9.80 mmol, 2.06M in THF) over 3 min. The reaction mixture was warmed to 0° C. and was kept at that temperature for 1 h. Saturated NH$_4$Cl was added (5 mL), and the heterogeneous mixture was poured into saturated NaHCO$_3$ (100 mL) and was washed with EtOAc (2×100 mL). The organic layer was dried (Na$_2$SO$_4$), concentrated and purified by flash chromatography (5% EtOAc/Hexane), to isolate the desired isomer N as a colorless oil (374 mg, 44%). Rƒ=0.23 (10% EtOAc/Hexane).

$^1$H NMR (400 MHz, CDCl$_3$) δ 7.13–7.35 (m, 10H), 3.74–3.84 (m, 6H), 2.88 (d, 1H, J=13.7 Hz), 2.80 (d, 1H, J=13.4 Hz), 2.77 (d, 1H, J=11.4 Hz), 2.75 (d, 1H, J=13.4 Hz), 2.62 (d, 1H, J=11.4 Hz), 2.47 (dd, 1H, J=13.7, 10.9 Hz), 2.10 (dd, J=7.2, 4.9 Hz), 1.99 (d, 1H, J=11.4 Hz), 1.90 (d, 1H, J=11.5 Hz), 1.85 (d, 1H, J=11.4 Hz), 1.85 (s, 1H), 1.70–1.78 (m, 4H), 0.99 (t, 9H, J=8.0 Hz), 0.86 (d, 3H, J=6.2 Hz), 0.85 (d, 3H, J=6.2 Hz), 0.65 (q, 6H, J=8.0 Hz).

Compound 16

Step 8:

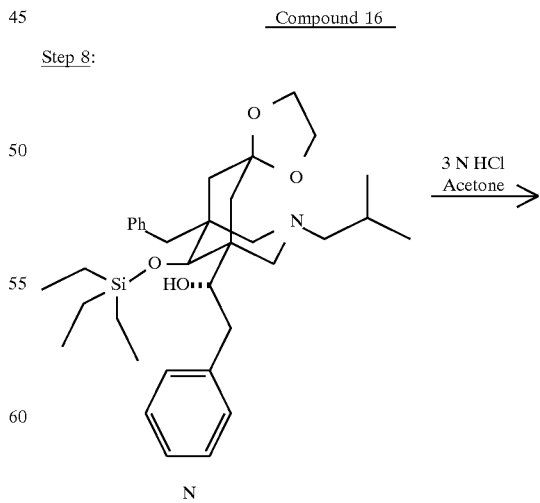

-continued
Compound 16

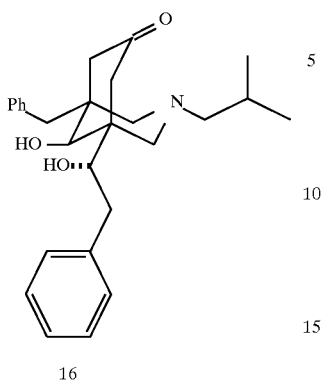

16

Aqueous HCl (3N, 10 mL) was added to a solution of N (374 mg, 0.64 mmol) in acetone (10 mL). The mixture was heated at 65° C. for 16 h. After cooling to 23° C., the reaction mixture was slowly poured into saturated NaHCO₃ (75 mL). The biphasic system was extracted with EtOAc (2×150 mL), and the combined organic layers were dried (Na₂SO₄), and concentrated to give 16 as a white solid (265 mg, 99%). Rƒ=0.13 (30% EtOAc/Hexane), mp=138°–141° C.

$^1$H NMR (CDCl₃) δ 7.16–7.37 (m, 10H), 3.88 (s, 1H), 3.83 (s, 1H), 3.66 (d, 1H, J=11.2 Hz), 2.98 (d, 1H, J=15.9 Hz), 2.90 (d, 1H, J=13.4 Hz), 2.69 (m, 1H), 2.81 (s, 2H), 2.65 (d, 2H, J=13.9 Hz), 2.48 (d, 2H, J=11.4 Hz), 2.00–2.09 (m, 5H), 1.91 (d, 1H, J=11.5 Hz), 1.53–1.66 (m, 1H), 0.79 (d, 3H, J=6.4 Hz), 0.78 (d, 3H, J=6.6 Hz). Anal. Calcd for C₂₇H₃₅NO₃.0.30 H₂O: C, 75.95; H, 8.40; N, 3.28. Found: C, 75.91; H, 8.30; N, 3.55. HRMS calcd for C₂₇H₃₅NO₃ 422.2695, found 422.2693.

EXAMPLE 3

5(RS)-methylpheny-9(RS)-hydroxy-1(RS)-((1'-hydroxy)-2'-phenyl)-ethyl-3-benzyl-3-azabicyclo[3.3.1]nonan-7-one (Compound 18), Table II

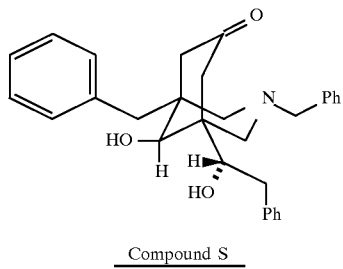

Compound S

Step 1:

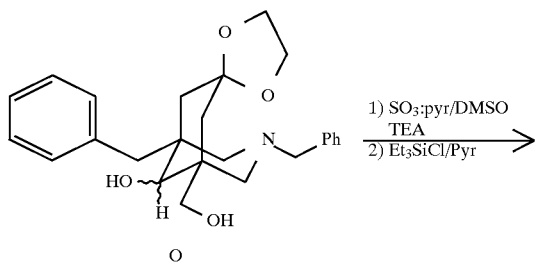

-continued

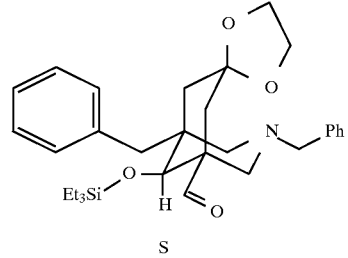

S

A mixture of diols (162 mg, 0.396 mmol), and SO₃.pyridine complex (189 mg, 1.19 mmol) were dissolved in dry DMSO (4 mL). Triethylamine (0.34 mL) was then added dropwise via syringe. The reaction was allowed to proceed for 1.5 hours at which point it was poured into saturated NH₄Cl solution. The aqueous phase was extracted with EtOAc (2×50 mL). The organics were combined and washed with H₂O, NaCl and dried (Na₂SO₄). The extracts were filtered, concentrated to an oil (147 mg) that was used in the next step without purifcation. The crude mixture of hydroxyaldehydes were dissolved in pyridine (6 mL) and treated with triethylsilyl chloride (0.34 mL, 20 mmol) and catalytic amounts of 4-dimethylaminopyridine (10 mg). The reaction was allowed to proceed at 60° C. for 16 hours. The reaction was cooled to room temperature and the volatiles were removed via rotorevaporater. The residue was diluted with Et₂O (75 mL) and washed succesively with NaHCO₃, H₂O and NaCl. The organics were dried over Na₂SO₄ and concentrated. Flash chromatography (9:1, Hexanes/EtOAc) gave the desired compound (S) as an oil (62 mg, 28%).

$^1$H NMR (400 MHz, CDCl₃) δ 9.54 (s, 1H), 7.14–7.31 (m, 10H), 3.82 (m, 5H), 3.54 (AB, JAB=13Hz, 2H), 2.78 (AB, JAB=13.5 Hz, 2H), 2.71 (m, 2H), 2.19 (dd, J=11.7 Hz, 3.1 Hz, 1H), 1.96 (m, 4H), 0.99 (t, J =8 Hz, 9H), 0.65 (q, J=8 Hz, 6H).

Compound 18

Step 2:

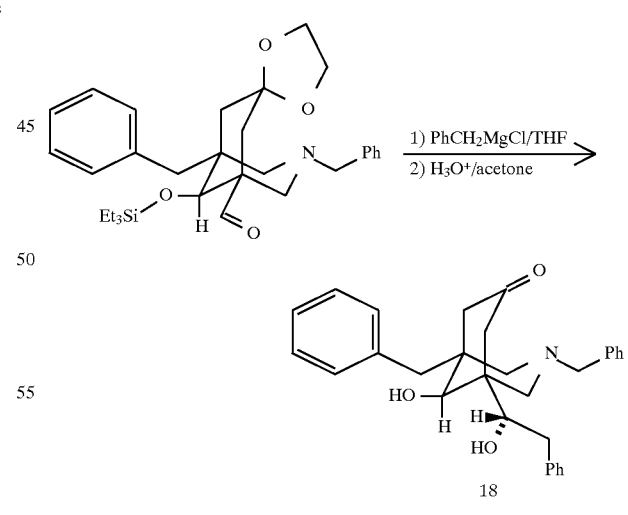

18

A solution of benzyl magnesium chloride in THF (2.06M, 0.2 mL) was added to a solution of the aldehyde S from step 1 (61 mg, 0.109 mmol) in dry THF (1 mL) at −78° C. The reaction was stirred at −78° C. for 1.5 hours then slowly warmed to room temperature and excess Grignard was quenched with saturated NH₄Cl solution. The reaction was diluted with EtOAc (60 mL) and washed with NH₄Cl, NaCl and dried over Na$_2$SO$_4$. The material was immediately hydrolyzed in THF/1N HCl (4:1, 2.5 mL). The desired compound was purified via flash chromatography 1:1 EtOAc/Hexanes and crystallized from Et$_2$O/Hexanes. m.p. 145.5°–147° C.

$^1$H NMR (400 MHz, CDCl$_3$) δ 7.17–7.34 (m, 15H), 3.90 (d, J=9.9 Hz, 2H), 3.58 (m, 2H), 3.35 (d, J=13.4 Hz, 1H), 3.00 (d, J=15.7 Hz, 1H), 2.43–2.84 (m, 5H), 2.81 (AB, JAB=13.5 Hz, 2H), 2.0–2.12 (m, 3H). Low resolution FAB Mass spec (M+ +1)m/z 456. Anal calc'd for C$_{30}$H$_{33}$NO$_3$.0.65 H$_2$O: C, 77.10; H, 7.40, N, 3.0. Found: C, 71.15; H, 7.24; N, 3.10.

EXAMPLE 4

5(RS)-methylpheny-9(RS)-hydroxy-1(RS)-((1'-hydroxy)-2'-(2'''-(tetra-hydro-1,2-thiazine 1,1-dioxide))-ethyl-3-benzyl-3-azabicyclo[3.3.1]nonan-7-one (Compound 23), Table II

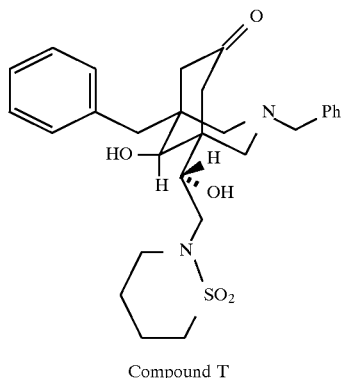

Compound T

Step 1:

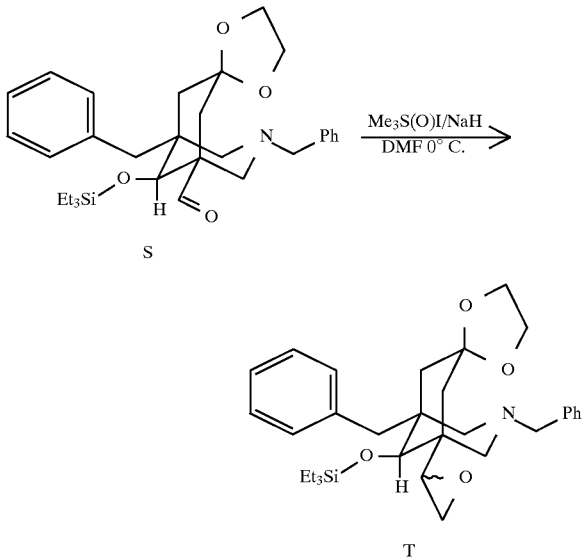

A solution of trimethylsulfoxonium iodide (298 mg, 1.35 mmol), NaH (32 mg, 1.35 mmol) and DMF (4 mL) were stirred at 0° C. for 30 minutes. A solution of aldehyde S from above (152 mg, 0.2709 mmol) in DMF (0.5 mL) was added via syringe. The transfer was completed with two washings of DMF (2×0.25 mL). The reaction was stirred at 0° C. for 1 hour and quenched with a saturated solution of NH$_4$Cl. The reaction was poured into NaCl and extracted with Et$_2$O (3×35 mL). The organics were combined and washed with H$_2$O, NaCl, and dried over Na$_2$SO$_4$. Flash chromatography using 8:1 Hexane/EtOAc gave 68 mg of one diastereomer and 25 mg of a second diastereomer (both oils).

Major more polar isomer $^1$H NMR (400 MHz, CDCl$_3$), δ 7.14–7.3 (m, 10H), 3.81 (m, 4H), 3.60 (s, 1H), 3.50 (AB, JAB=13.2 Hz, 2H), 2.67 (br t, J=3 Hz, 1H), 2.78 (AB, JAB=13.5 Hz, 2H), 2.72 (d, J=11.4 Hz, 1H), 2.66 (m, 2H), 2.60 (d, J=11.4 Hz, 1H), 1.96 (d, J=11.4 Hz, 1H), 1.89 (d, J=11.5 Hz, 1H), 1.82 (dd, J=11.5 Hz, 2.9 Hz, 1H), 1.76 (dd, J=11.4 Hz, 9.4 Hz, 1H), 1.53 (dd, J=11.9 Hz, 3.1 Hz, 1H), 1.00 (t, J=7.5 Hz, 9H), 0.65 (q, J=7.5 Hz, 6H).

Minor less polar isomer $^1$H NMR (400 MHz, CDCl$_3$), δ 7.10–7.32 (m, 10H), 3.79 (m, 4H), 3.50 (AB, JAB=13.2 Hz, 2H), 3.23 (s, 1H), 2.62–2.77 (m, 7H), 1.80–1.96 (m, 4H), 1.70 (dd, J=11.5 Hz, 2.5 Hz, 1H), 0.98 (t, J=7.7 Hz, 9H), 0.64 (q, J=7.7 Hz, 6H).

Compound 23

Step 2:

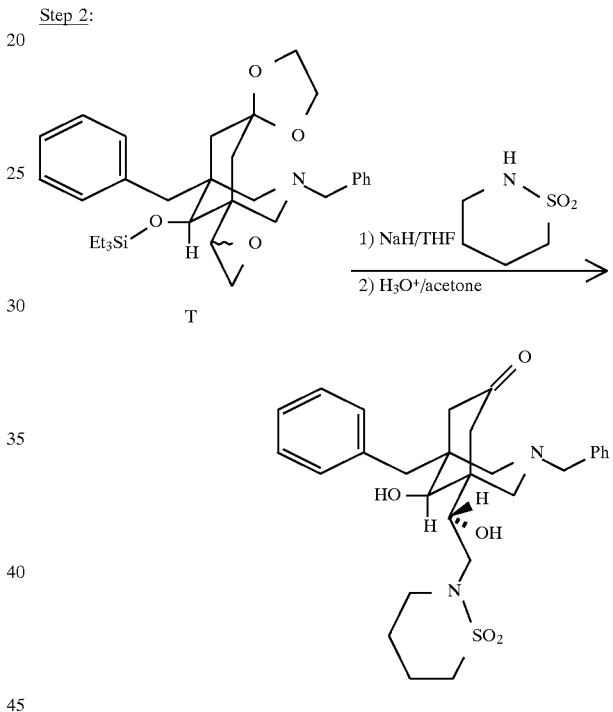

NaH (8 mg, 60 wt % in mineral oil, 200 μmol) was added to a solution of tetrahydro-1,2-thiazine-1,1-dioxide (34 mg, 250 μmol) in N,N-dimethylformamide (1 mL) and the resulting mixture was stirred at 23° C. for 30 min. A solution of T (27 mg, 50 μmol) in N,N-dimethylformamide (1 mL) was added and the mixture was heated at 65° C. for 16 h. The reaction was cooled to room temperature and NH$_4$Cl solution (2 mL) was added. The reaction mixture was poured into water (50 mL) and the resulting aqueous mixture was extracted with Et$_2$O (2×50 mL). The combined organic extracts were washed with water (25 mL), dried (Na$_2$SO$_4$), and concentrated to give a mixture of starting material and desired product which was used without further purification.

A solution containing the crude reaction mixture from above (30 mg) in acetone (3 mL) was treated with aqueous hydrochloric acid (3N, 3 mL) and the colorless solution was heated at 65° C. for 12 h. The reaction mixture was cooled to room temperature and slowly poured into saturated NaHCO$_3$ (25 mL). The resulting suspension was washed with EtOAc (30 mL) and the organic layer was dried (Na$_2$SO$_4$), and concentrated to give a crude oil which was purified by flash chromatography (70% EtOAc/Hexane) to give 23 as a white solid (15 mg, 58% for 2 steps). R$f$=0.13 (70% EtOAc/Hexane), mp=163°–164° C.

$^1$H NMR (400 MHz, CDCl$_3$) δ 7.13–7.33 (m, 10H), 3.80 (bs, 1H), 3.63 (bd, 1H, J=10.1 Hz), 3.59 (bs, 1H), 3.51 (d, 1H, J=13.4 Hz), 3.21–3.39 (m, 4H), 3.01–3.06 (m, 3H), 2.86 (d, 1H, J=15.6 Hz), 2.79 (d, 1H, J=13.4 Hz), 2.73 (d, 1H, J=13.4 Hz), 2.66 (d, 1H, J=15.6 Hz), 2.53 (dd, 1H, J=11.3, 1.8 Hz), 2.37 (dd, 1H, J=10.9, 1.9 Hz), 2.20 (quintet, 2H, J=6.0 Hz), 1.93–2.09 (m, 4H), .1.64–1.66 (m, 2H). Anal calcd. for C$_{28}$H$_{36}$N$_2$SO$_5$.0.80 H$_2$O: C, 63.81; H, 7.19; N, 5.31. Found: C, 63.81; H, 7.02; N, 5.18; HRMS calcd for C$_{28}$H$_{36}$N$_2$SO$_5$ 513.2423, found 513.2437.

EXAMPLE 5

5(RS)-methylpheny-9(RS)-hydroxy-1(RS)-((1'-hydroxy)-2'-(2"-amino)-phenyl)-ethyl-3-benzyl-3-azabicyclo[3.3.1] nonan-7-one (Compound 20), Table II

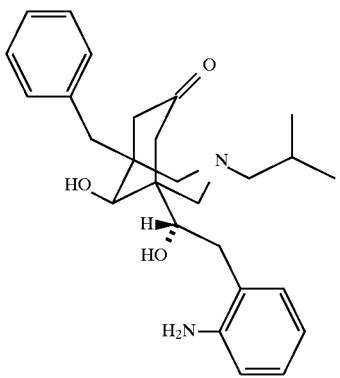

A. Step 1:

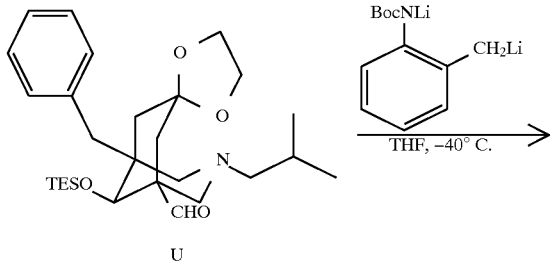

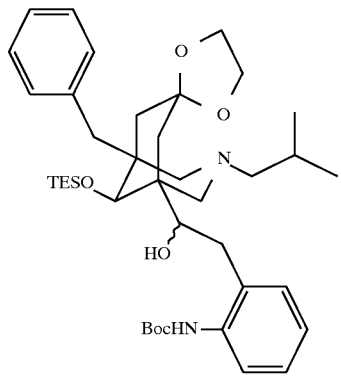

V

A solution of tert-butyllithium in pentane (1.7M, 3.00 mL, 5.10 mmol, 9.64 equiv) was added over 1 min to a solution of tert-butyl 2-methylcarbanilate (515 mg, 2.48 mmol, 4.69 equiv) in THF (3.5 mL) at −40° C. The resulting bright yellow mixture was stirred at −40° C. for 15 min, then a solution of the aldehyde, U, (300 mg, 0.529 mmol, 1 equiv) in THF (4 mL) was added. The resulting mixture was warmed to 0° C. and was held at that temperature for 15 min. The product solution was diluted with pH 7 phosphate buffer solution (100 mL), and the resulting aqueous mixture was extracted with EtOAc (2×75 mL). The combined organc layers were dried over Na$_2$SO$_4$ and were concentrated. The residue was purified by flash chromatography (5% EtOAc in hexanes initially, grading to 20% ethyl acetate in hexanes) to provide the desired alcohol as a colorless oil (85 mg, 21%) as well as the undesired diastereomeric alcohol as a colorless oil (81 mg, 20%).

$^1$H NMR (400 MHz, CDCl$_3$), δ 7.78 (br s, 1H, NH), 7.59 (br d, 1H, J=7.9 Hz, ArH), 7.32–7.07 (m, 7H, PhH and ArH), 7.00 (br t, 1H, J=7.3 Hz, ArH), 3.81 (m, 2H, OCH$_2$CH$_2$O), 3.75 (m, 2H, OCH$_2$CH$_2$O), 3.67 (s, 1H, (CH$_3$CH$_2$)$_3$SiOCH), 3.11 (br d, 1H, J=5.1 Hz, HOCH), 2.77–2.56 (m, 6H, PhCH$_2$, ArCH$_2$ and NCH$_2$), 2.10 (m, 2H, NCH$_2$CH(CH$_3$)$_2$ and NCH$_2$ or CH$_2$), 2.03 (d, 1H, J=11.2 Hz, NCH$_2$ or CH$_2$), 1.94 (d, 1H, J=11.4 Hz, NCH$_2$ or CH$_2$), 1.84 (m, 2H, NCH$_2$CH(CH$_3$)$_2$ and NCH$_2$ or CH$_2$), 1.71 (m, 3H, NCH$_2$ and/or CH$_2$ and NCH$_2$CH(CH$_3$)$_2$, 1.52 (s, 9H, OC(CH$_3$)$_3$), 0.98 (t, 9H, J=7.9 Hz, (CH$_3$CH$_2$)$_3$Si), 0.86 (d, 3H, J=6.4 Hz, CH(CH$_3$)$_2$), 0.85 (d, 3H, J=6.4 Hz, CH(CH$_3$)$_2$), 0.64 (q, 6H, J=7.9 Hz, (CH$_3$CH$_2$)$_3$Si).

TLC (20% EtOAc-hexanes), Rf: desired alcohol: 0.36 (UV), undesired alcohol: 0.44 (UV)

Step 2:

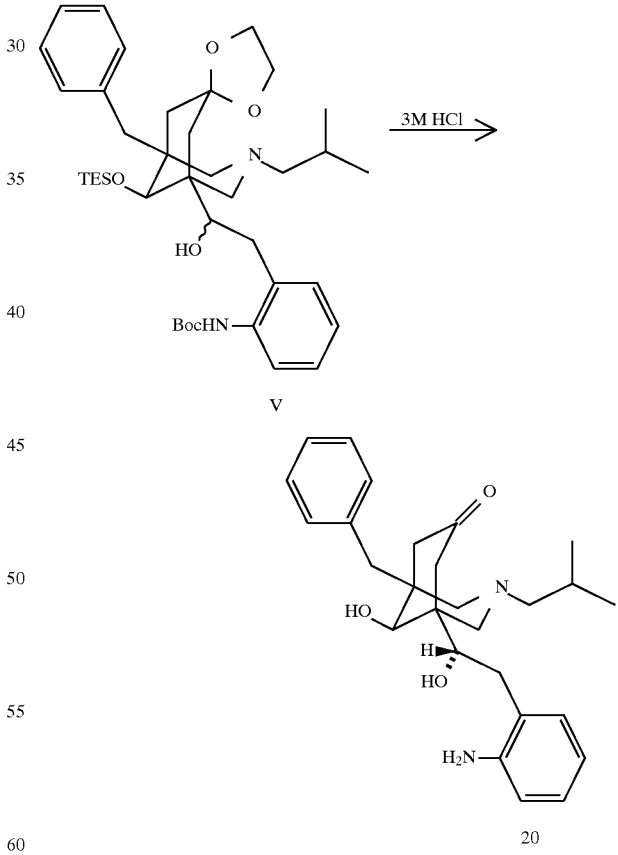

A solution of the ketal (80 mg, 0.11mmnol) in a mixture of aqueous 3M HCl solution (10 mL) and acetone (10 mL) was heated at 60° C. for 16 h. After cooling to 23° C., the product solution was carefully diluted with aqueous saturated NaHCO$_3$ solution (100 mL). The resulting aqueous mixture was extracted with EtOAc (2×50 mL). The combined organic layers were dried over Na$_2$SO$_4$ and were concentrated. The residue was purified by flash chromatography (40% EtOAc in Hexanes initially, then 40% Hexanes in EtOAc) to afford the product ketone as a colorless oil (31 mg, 67%). The product oil was triturated with Et$_2$O to produce a white crystalline solid (mp=164°–165° C.).

$^1$H NMR (400 MHz, CDCl$_3$) δ 7.32–7.12 (m, 5H, PhH), 7.08 (td, 1H, J=7.6, 1.4 Hz, ArH), 7.00 (dd, 1H, J=7.5, 1.3 Hz, ArH), 6.80 (td, 1H, J=7.5, 1.1 Hz, ArH), 6.71 (dd, 1H, J=7.9, 0.7 Hz, ArH), 3.98 (br s, 1H, OH), 3.88 (br s, 1H, HOCH), 3.74 (br s, 2H, NH), 3.68 (dd, 1H, J=10.4, 1.7 Hz, HOCH), 2.87 (d, 1H, J=15.9 Hz, NCH$_2$), 2.77 (m, 3H, PhCH$_2$ and ArCH$_2$), 2.65 (br d, 1H, J=14.7 Hz, ArCH$_2$), 2.62 (d, 1H, J=16.1 Hz, NCH$_2$), 2.46 (m, 2H, NCH$_2$CH(CH$_3$)$_2$), 2.04 (m, 5H, NCH$_2$ and CH$_2$), 1.91 (d, 1H, J=11.5 Hz, NCH$_2$ or CH$_2$), 1.61 (m, 1H, NCH$_2$CH(CH$_3$)$_2$), 0.77 (d, 3H, J=6.6 Hz, CH(CH$_3$)$_2$), 0.76 (d, 3H, J=6.4 Hz, CH(CH$_3$)$_2$). High-Res MS (FAB): Calcd for C$_{27}$H$_{36}$N$_2$O$_3$ [M+H]$^+$: 437.2804 Found: 437.2813 Calcd for C$_{27}$H$_{36}$N$_2$O$_3$: C, 74.28; H, 8.31; N, 6.42. Found: C, 74.28; H, 8.34; N, 6.52; TLC (40% EtOAc-hexanes), R$_f$:0.06

While the foregoing specification teaches the principles of the present invention, with examples provided for the purpose of illustration, it will be understood that the practice of the invention emcompasses all of the usual variations, adaptations, or modifications, as come within the scope of the following claims and its equivalents.

What is claimed is:

1. A compound of the formula:

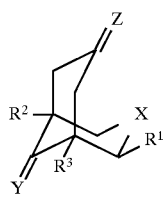

wherein

X is —O—, —NH—, —NR$^4$— or —S—;

Y is =O, or forms, with the carbon to which it is attached,

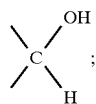

Z is =O, or forms, with the carbon to which it is attached,

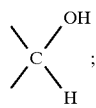

R$^1$ is
 a) H;
 b) C$_{1-4}$ alkyl;
 c) C$_{3-7}$ cycloalkyl;
 d) aryl, unsubstituted or substituted one or more times with hydroxy;
 e) CH$_2$R$^5$; or
 f) 5–7 membered heterocycle; and R$^2$ is
 a) C$_{1-4}$ alkyl;
 b) aryl, unsubstituted or substituted with aryl;
 c) CH$_2$R$^6$; or
 d) heterocycle; and R$^3$ is
 a) CH(OH)R$^7$; or
 b) CH(NH$_2$)R$^7$; and R$^4$ is
 a) C$_{1-4}$ alkyl;
 b) C$_{3-6}$ cycloalkyl;
 c) aryl unsubstituted or substituted with halo or with C$_{1-4}$ alkyl unsubstituted or substituted one or more times with hydroxy;
 d) CH$_2$R$^1$; or
 e) 5–7 member ed heterocycle; and R$^5$ is
 a) C$_{1-4}$ alkyl; or
 b) aryl; and R$^6$ is
 a) C$_{1-4}$ alkyl;
 b) aryl unsubstituted or substituted with halo or with C$_{1-4}$ alkyl unsubstituted or substituted one or more times with hydroxy; or
 c) 5–7 membered heterocycle; and R$^7$ is
 a) H;
 b) C$_{1-4}$ alkyl;
 c) aryl unsubstituted or substituted with amino;
 d) C$_{1-3}$ alkylaryl unsubstituted or substituted with amino; or
 e) 5–7 membered heterocycle;

or pharmaceutically acceptable salt thereof.

2. A compound of the formula

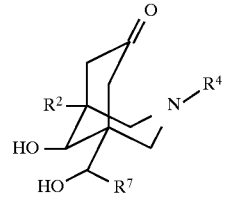

wherein

R$^2$ is C$_{1-4}$ alkylene-aryl; and

R$^4$ is C$_{1-4}$ alkyl, unsubstituted or substituted with aryl, C$_{3-6}$ cycloalkyl, or 5–7 membered heterocycle;

R$^7$ is H, benzyl unsubstituted or substituted with amino; or pharmaceutically acceptable salt thereof.

3. The compound of claim 1 of the formula

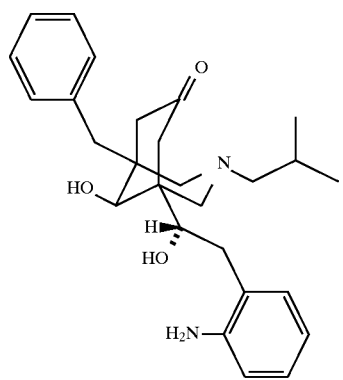

or pharmaceutically acceptable salts thereof.

4. The compound of claim 1 of the formula

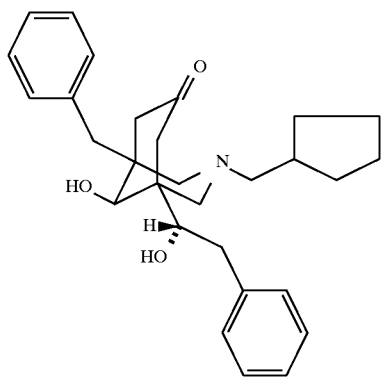

or pharmaceutically acceptable salts thereof.

5. A pharmaceutical composition comprising the compound of claim 1, and a pharmaceutically acceptable carrier.

6. The pharmaceutical composition of claim 5, for use in the treatment of and the delaying of the onset of AIDS, in the prevention of infection by HIV, in the treatment of infection of HIV, or in the inhibition of HIV protease.

7. A method of treating and delaying the onset of AIDS, comprising administering to a mammal in need of such treatment an effective amount of a compound of claim 1.

8. A method of preventing infection by HIV, comprising administering to a mammal in need of such treatment an effective amount of a compound of claim 1.

9. A method of treating infection by HIV, comprising administering to a mammal in need of such treatment an effective amount of a compound of claim 1.

10. A method of inhibiting HIV protease, comprising administering to a mammal in need of such treatment an effective amount of a compound of claim 1.

11. A combination of compounds, which is the compound of claim 3 with (−) 6-chloro-4(S)-cyclopropylethynyl-4(S)-trifluoromethyl-1,4-dihydro-2H-3,1-benzoxazin-2-one, and, optionally, AZT or ddI or ddC.

12. A combination of compounds, which is

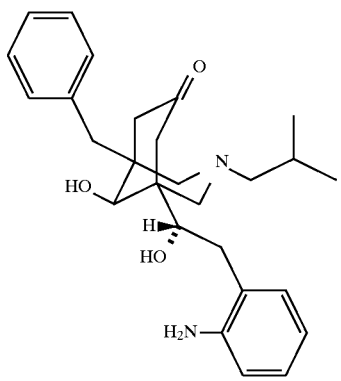

or

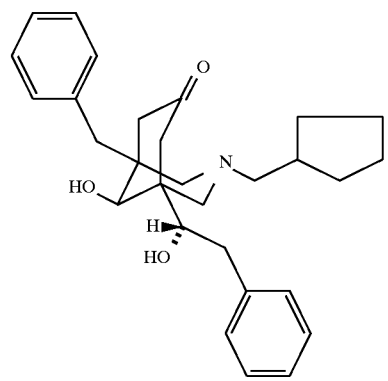

or pharmaceutically acceptable salts thereof, and any of AZT or ddI or ddC.

13. A combination of compounds, which is the compound of claim 4 with (−) 6-chloro-4(S)-cyclopropylethynyl-4(S)-trifluoromethyl-1,4-dihydro-2H-3,1-benzoxazin-2-one, and optionally, AZT or ddI or ddC.

* * * * *